(12) United States Patent
Aoki et al.

(10) Patent No.: US 8,524,918 B2
(45) Date of Patent: Sep. 3, 2013

(54) ATROPISOMER OF PYRROLE DERIVATIVE

(75) Inventors: Kazumasa Aoki, Tokyo (JP); Hiroyuki Tsuruoka, Kanagawa (JP); Noriyuki Hayashi, Tokyo (JP); Juri Yoshida, Tokyo (JP); Yusuke Asoh, Kanagawa (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 193 days.

(21) Appl. No.: 12/576,091

(22) Filed: Oct. 8, 2009

(65) Prior Publication Data

US 2010/0093826 A1   Apr. 15, 2010

Related U.S. Application Data

(63) Continuation of application No. PCT/JP2008/056907, filed on Apr. 8, 2008.

(30) Foreign Application Priority Data

Apr. 9, 2007   (JP) .................................. 2007-101938

(51) Int. Cl.
*C07D 207/30* (2006.01)
*A61K 31/40* (2006.01)

(52) U.S. Cl.
USPC .......................................... 548/537; 514/423

(58) Field of Classification Search
USPC .......................................... 548/537; 514/423
See application file for complete search history.

(56) References Cited

U.S. PATENT DOCUMENTS

| | | | |
|---|---|---|---|
| 6,323,208 B1 | 11/2001 | Chenard | |
| 6,939,968 B2 | 9/2005 | Vrudhula | |
| 2008/0234270 A1* | 9/2008 | Canne Bannen et al. | .. 514/235.5 |

FOREIGN PATENT DOCUMENTS

WO   2006/012642 A2   2/2006

OTHER PUBLICATIONS

Boiadjiev, S.E., and D.A. Lightner, "Stable Monopyrrole Atropisomers," Monatshefte für Chemie 133(11):1469-1480, Oct. 2002.
Communication Pursuant to Article 94(3) EPC mailed Mar. 30, 2011, issued in corresponding European Application No. EP 08 740 010.7, filed Apr. 8, 2008, 3 pages.
Eliel, E.L., et al., "Chirality in Molecules Devoid of Chiral Centers: Biphenyls. Atropisomerism," Stereochemistry of Organic Compounds, John Wiley & Sons, New York, Jan. 1994, pp. 1142-1148.

European Search Report issued Jul. 9, 2010, in corresponding European Application No. 08740010, filed Apr. 8, 2008, 6 pages.
Mannschreck A., et al., "The Enantiomers of Methaqualone and Their Unequal Anticonvulsive Activity," European Journal of Medicinal Chemistry 19(4):381-383, Jan. 1984.
Booth, R.E., et al., "Aldosterone," Advances in Physiology Education 26(1):8-20, Mar. 2002.
Murakami, H., "Separation of Enantiomers (Kogaku Iseitai no Bunri): 18. Utilization of Optically Active Compounds," Kikan Kagaku Sosetsu (Elements of Chemistry, Quarterly Review) 6:212-213, 1989.
Wermuth, C.G., "Specific Substituent Effects" in C.G. Wermuth (ed.), The Practice of Medicinal Chemistry (Saishin Soyaku Kagaku) [translated under the supervision of Hiroshi Nagase], Technomics, Inc., Tokyo, 1998, Chap. 17, p. 358.
International Search Report mailed Jun. 3, 2008, issued in corresponding International Application No. PCT/JP2008/056907, filed Apr. 8, 2008.
Canadian Intellectual Property Office communication mailed Jun. 16, 2011, issued in corresponding Canadian Application No. 2,683,059, filed Apr. 8, 2008, 2 pages.
Bringmann, G., et al., "Atroposelective Synthesis of Axially Chiral Biaryl Compounds," Angewandte Chemie 44(34):5384-5427, Aug. 2005.
Communication Pursuant to Article 94(3) EPC, mailed Mar. 29, 2012, issued in corresponding EP Application No. 08 740 010.7, filed Apr. 8, 2008, 3 pages.
Le Gac, S., et al., "Stereoselective Synthesis of New Classes of Atropisomeric Compounds Through a Tandem Michael Reaction-Azacyclization Process—Part 2," Tetrahedron: Asymmetry 15(1):139-145, Jan. 2004.

* cited by examiner

*Primary Examiner* — Shirley V Gembeh
(74) *Attorney, Agent, or Firm* — Christensen O'Connor Johnson Kindness PLLC

(57) ABSTRACT

[Object] A prophylactic or therapeutic agent for a cardiovascular disease is provided.
[Means for Resolution] An atropisomer of a compound represented by the following general formula (I):

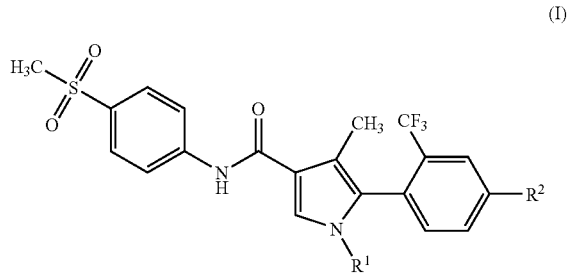

(I)

(wherein $R^1$ is a C1-C3 alkyl group or a hydroxy-C1-C3 alkyl group; and $R^2$ is a hydrogen atom or a C1-C3 alkoxy group).

6 Claims, No Drawings

ATROPISOMER OF PYRROLE DERIVATIVE

CROSS-REFERENCES TO RELATED APPLICATIONS

This application is a continuation of International Application No. PCT/JP2008/056907, filed Apr. 8, 2008, which claims priority from Japanese Application No. 2007-101938, filed Apr. 9, 2007. Each application is incorporated herein by reference in its entirety.

TECHNICAL FIELD

The present invention relates to an atropisomer of a pyrrole derivative having excellent mineralocorticoid receptor antagonistic activity and to a prophylactic or therapeutic agent for hypertension, angina pectoris, acute coronary syndrome, congestive heart failure, nephropathy, arteriosclerosis, cerebral infarction, fibrosis or primary aldosteronism containing the same.

BACKGROUND ART

The mineralocorticoid receptor (MR) (aldosterone receptor) is known to play an important role in regulating electrolyte balance and blood pressure in the body (see, for example, Non-patent Document 1), and mineralocorticoid receptor antagonists such as spironolactone and eplerenone both of which have a steroidal structure are known to be useful for the treatment of hypertension and heart failure.

Further, as a mineralocorticoid receptor antagonist having a nonsteroidal backbone, a pyrrole derivative described in WO 2006/012642 (Patent Document 1) is known. However, an atropisomer of a compound having the general formula (I) of the invention is not known.

[Non-patent Document 1] Advances in Physiology Education, 26(1): 8-20 (2002)

[Patent Document 1] WO 2006/012642

DISCLOSURE OF THE INVENTION

Problems that the Invention is to Solve

The present inventors made efforts to develop an excellent prophylactic or therapeutic agent for cardiovascular disease and conducted intensive studies of pharmacological activities of various pyrrole derivatives. As a result, they found that atropisomers exist for a compound having the general formula (I), and that one of the atropisomers shows significantly excellent mineralocorticoid receptor antagonistic activity (in vitro and in vivo activities) and sustainability of agent effect, and further has excellent properties with respect to solubility, oral absorption, blood concentration, metabolic stability, safety and the like, and is useful as a pharmaceutical, preferably, as a prophylactic or therapeutic agent (particularly a therapeutic agent) for a disease such as hypertension, angina pectoris, acute coronary syndrome, congestive heart failure, nephropathy, arteriosclerosis, cerebral infarction, fibrosis, primary aldosteronism or heart disease, more preferably, for congestive heart failure, nephropathy, hypertension or the like, particularly preferably for hypertension, and thus, the invention has been completed.

Means for Solving the Problems

The invention provides an atropisomer of a compound having the general formula (I), having excellent mineralocorticoid receptor antagonistic activity and a pharmaceutical containing the same [a prophylactic or therapeutic agent (particularly a therapeutic agent) for hypertension, angina pectoris, acute coronary syndrome, congestive heart failure, nephropathy, arteriosclerosis, cerebral infarction, fibrosis, primary aldosteronism or heart disease (more preferably, for congestive heart failure, nephropathy and hypertension; particularly preferably for hypertension)].

That is, the invention relates to (1) an atropisomer of a compound represented by the following general formula (I):

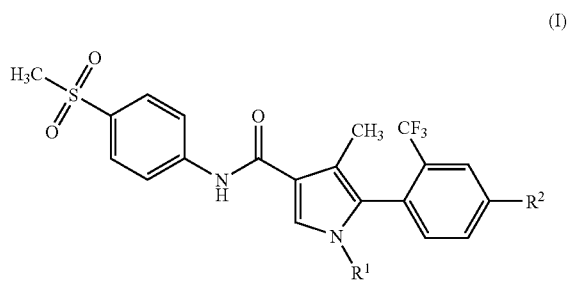

(wherein $R^1$ is a C1-C3 alkyl group or a hydroxy-C1-C3 alkyl group; and $R^2$ is a hydrogen atom or a C1-C3 alkoxy group).

Further, the invention relates to the following aspects:

(2) an atropisomer which, between a pair atropisomers each of a compound represented by the general formula (I), shows the more potent mineralocorticoid receptor antagonistic activity;

(3) the atropisomer according to (1) or (2), wherein $R^1$ is a methyl group or a 2-hydroxyethyl group;

(4) the atropisomer according to any one of (1) to (3), wherein $R^2$ is a hydrogen atom or a methoxy group;

(5) the atropisomer according to (1) or (2), wherein $R^1$ is a 2-hydroxyethyl group and $R^2$ is a hydrogen atom;

(6) the atropisomer according to (1) or (2), wherein $R^1$ is a methyl group and $R^2$ is a hydrogen atom;

(7) the atropisomer according to (1) or (2), wherein $R^1$ is a 2-hydroxyethyl group and $R^2$ is a methoxy group;

(8)(−)-1-(2-hydroxyethyl)-4-methyl-N-[4-(methylsulfonyl)phenyl]-5-[2-(trifluoromethyl)phenyl]-1H-pyrrole-3-carboxamide;

(9)(+)-1,4-dimethyl-N-[4-(methylsulfonyl)phenyl]-5-[2-(trifluoromethyl)phenyl]-1H-pyrrole-3-carboxamide;

(10)(−)-1-(2-hydroxyethyl)-5-[4-methoxy-2-(trifluoromethyl)phenyl]-4-methyl-N-[4-(methylsulfonyl)phenyl]-1H-pyrrole-3-carboxamide;

(11) a pharmaceutical containing the atropisomer according to any one of (1) to (10) as an active ingredient;

(12) a prophylactic or therapeutic agent for a cardiovascular disease, containing the atropisomer according to any one of (1) to (10) as an active ingredient;

(13) a prophylactic or therapeutic agent for hypertension, containing the atropisomer according to any one of (1) to (10) as an active ingredient;

(14) a pharmaceutical composition comprising the atropisomer according to any one of (1) to (10) and a pharmacologically acceptable carrier.

Examples of the "C1-C3 alkyl group" in the above-mentioned general formula (I) include linear or branched alkyl groups having 1 to 3 carbon atoms such as a methyl group, an ethyl group, an n-propyl group and an isopropyl group, and preferred is a methyl group.

The "hydroxy-C1-C3 alkyl group" in the above-mentioned general formula (I) means a group formed by substituting the above-mentioned "C1-C3 alkyl group" with one hydroxy group. Examples thereof include a 2-hydroxyethyl group, a 2-hydroxy-1-methylethyl group, a 2-hydroxypropyl group and a 3-hydroxypropyl group, and preferred is a 2-hydroxyethyl group.

The "C1-C3 alkoxy group" in the above-mentioned general formula (I) means a C1-C3 alkyloxy group formed from the above-mentioned "C1-C3 alkyl group" and denotes a linear or branched alkoxy group having 1 to 3 carbon atoms such as a methoxy group, an ethoxy group, an n-propoxy group or an isopropoxy group, and preferred is a methoxy group.

The "atropisomer" refers to a structural isomer based on axial or planar chirality resulting from restricted rotation in the molecule. The compound having the general formula (I) of the invention has two atropisomers derived from axial chirality which result from restricted rotation about the bond between the phenyl group substituted at the ortho position with a trifluoromethyl group and the substituted pyrrole ring, due to steric hindrance. The "atropisomer" of the invention is either one of the two atropisomers of the compound having the general formula (I). However, it is preferably the atropisomer which shows the more excellent pharmacological activity, stability, in vivo kinetics, safety and the like and has favorable properties as a pharmaceutical.

Advantage of the Invention

The atropisomer of a compound having the general formula (I) of the invention shows excellent mineralocorticoid receptor antagonistic activity and high plasma concentration and blood retention, is excellent in pharmacological activity and in vivo kinetics such as oral absorption, in vivo distribution and blood retention, and is also highly safe to organs such as kidney and liver. Further, the atropisomer of a compound having the general formula (I) of the invention is very stable. For example, even after the atropisomer is treated in methanol at room temperature for 7 days or in an acetonitrile-phthalic acid buffer at 60° C. for 4 hours, racemization was not observed.

Therefore, the atropisomer of a compound having the general formula (I) of the invention is useful as, for example, a pharmaceutical, and is particularly useful as a pharmaceutical for treating or preventing various cardiovascular diseases (preferably, hypertension, angina pectoris, acute coronary syndrome, congestive heart failure, nephropathy, arteriosclerosis, cerebral infarction, fibrosis, primary aldosteronism or heart disease).

BEST MODE FOR CARRYING OUT THE INVENTION

The atropisomer of a compound having the general formula (I) of the invention can be obtained by subjecting a racemic compound produced according to the method described in WO 2006/012642 to optical resolution. The optical resolution of the atropisomers is essentially the same as that of enantiomers due to sp3 asymmetric carbons or the like, and examples thereof include (1) a method by crystallization; (2) a method by enzymatic reaction; and (3) a method by chromatography. However, it is not limited to these. Hereinafter, representative optical resolution methods will be described in detail.

(1) Optical Resolution by Crystallization
(a) Preferential Crystallization Method
This is an optical resolution method using the property that a racemic mixture is spontaneously crystallized and can achieve optical resolution without requiring an asymmetric element.
(b) Diastereomer Method
This is a method in which a chiral compound called an optically resolving agent is allowed to act on a racemic compound to derivatize the compound into two diastereomers and these diastereomers are separated by fractional crystallization utilizing the difference in solubility between these diastereomers. The optical purity can be increased by repeating recrystallization. The objective enantiomer can be obtained by removing the resolving agent from a thus obtained single diastereomer. In the invention, a method in which fractional crystallization is performed after derivatization into covalent crystalline diastereomers is preferred. For example, in the case where a racemic alcohol is to be resolved, the racemic alcohol is derivatized into diastereomer esters with chiral carboxylic acids, from which a sparingly soluble diastereomer is taken out by recrystallization, and the thus obtained single diastereomer ester is hydrolyzed, whereby an optically active alcohol can be obtained.
(c) Inclusion Complex Method
This is an optical resolution method in which by using chiral host molecules and using one enantiomer of a racemic compound as a guest molecule, an inclusion complex is diastereoselectively formed and the optical purity is increased by recrystallization.
(d) Preferential Enrichment
This method is characterized in that enrichment of one enantiomer is caused in a mother liquor by recrystallization of racemic crystals. At the same time, crystals having a low optical purity with chirality opposite to that of the enantiomer in the mother liquor are deposited.
(2) Enzymatic Reaction
In the case where addition reaction to a racemic compound using an enzyme such as lipase is performed, the reaction of only one optically active compound proceeds depending on the substrate. This is a method which utilizes this property and in which, after the enzymatic reaction, the resulting product is separated and purified by recrystallization or chromatography, and thereafter the added functional group is removed under an appropriate condition to obtain the objective optically active compound. On the other hand, there is also a method in which a racemic compound is specifically modified in advance, and the modified racemic compound is subjected to enzymatic degradation reaction, and then, only one optically active compound is obtained in the same manner as described above.
(3) Direct Optical Resolution by Chromatography
When a stationary phase incorporating an asymmetric element to which a derivative of a sugar or the like is attached is used as a support, a difference in retention time of chromatography is caused thereby to enable resolution. Utilizing this property, direct resolution can be performed by high performance liquid chromatography with a chiral column. As the chiral column, for example, CHIRALPAK AD-H, CHIRALCEL OJ-RH (DAICEL) and the like can be exemplified.

In the case where the atropisomer of the invention is used as a pharmaceutical, the atropisomer of a compound having the above-mentioned general formula (I) can be administered as such or by mixing with an appropriate pharmacologically acceptable excipient, diluent or the like orally in the form of a tablet, a capsule, a granule, a powder, a syrup or the like, or parenterally in the form of an injection, a suppository, a plaster, a preparation for external use or the like.

These preparations are produced by well-known methods using an additive such as an excipient, a lubricant, a binder, a disintegrant, an emulsifier, a stabilizer, a flavoring agent or a diluent.

The amount of atropisomer used varies depending on symptoms, age or the like. However, it is preferably administered, in the case of oral administration to a human adult at a dose of 0.02 mg/kg (preferably 0.1 mg/kg) as a lower limit and 100 mg/kg (preferably 10 mg/kg) as an upper limit, in the case of parenteral administration at a dose of 0.002 mg/kg (preferably 0.01 mg/kg) as a lower limit and 10 mg/kg (preferably 1 mg/kg) as an upper limit one to six times a day depending on the symptom.

Hereinafter, the invention will be described in more detail with reference to Examples, Test Examples and Preparation Examples. However, the Scope of the Invention is not limited to these.

EXAMPLES

Example 1

(+/−)-1,4-dimethyl-N-[4-(methylsulfonyl)phenyl]-5-[2-(trifluoromethyl)phenyl]-1H-pyrrole-3-carboxamide The compound was synthesized by the method described in Example 16 of WO 2006/012642.

$^1$H-NMR (400 MHz, CDCl$_3$) δ: 7.90 (2H, d, J=8.6 Hz), 7.83-7.80 (3H, m), 7.70-7.58 (3H, m), 7.34 (1H, d, J=7.4 Hz), 7.30 (1H, s), 3.32 (3H, s), 3.05 (3H, s), 2.09 (3H, s).

HR-MS (ESI) calcd for C$_{21}$H$_{20}$F$_3$N$_2$O$_3$S [M+H]$^+$, required m/z: 437.1147, found: 437.1157.

Example 2

Optical Resolution of Compound of Example 1

Using 5 mL of an ethanol solution (4 to 6 mg/mL) of (+/−)-1,4-dimethyl-N-[4-(methylsulfonyl)phenyl]-5-[2-(trifluoromethyl)phenyl]-1H-pyrrole-3-carboxamide, resolution under the following HPLC conditions was performed 9 times, and 86 mg of Isomer A was obtained as a solid from a fraction containing Isomer A (t$_R$=11 min), and 87 mg of Isomer B was obtained as a solid from a fraction containing Isomer B (t$_R$=18 min).

For the separation by HPLC using a chiral column, the following conditions were used.

Apparatus: Shimadzu Class-VP System (LC-8/SCL-10AVP/SPD-10AVP); column: CHIRALPAK AD-H (2 cm×25 cm) semi-fractionation column; flow rate: 8.0 mL/min; elution solvent: ethanol (100%, isocratic); detection: UV (254 nm)

Isomer A: (−)-1,4-dimethyl-N-[4-(methylsulfonyl)phenyl]-5-[2-(trifluoromethyl)phenyl]-1H-pyrrole-3-carboxamide $[α]_D^{21}$: −18° (c=1.0, EtOH).
$^1$H-NMR (500 MHz, CDCl$_3$) δ: 7.92 (2H, d, J=8.3 Hz), 7.85-7.80 (3H, m), 7.69-7.64 (2H, m), 7.61 (1H, t, J=7.3 Hz), 7.35 (1H, d, J=7.3 Hz), 7.31 (1H, s) 3.33 (3H, s), 3.06 (3H, s), 2.10 (3H, s).

HR-MS (ESI) calcd for C$_{21}$H$_{20}$F$_3$N$_2$O$_3$S[M+H]$^+$, required m/z: 437.1147, found: 437.1138.

Retention time: 4.1 min.

For an analysis by HPLC using a chiral column, the following conditions were used. (Hereinafter, analysis was performed under the same conditions. The retention time was determined by chiral HPLC.)

Analysis apparatus: Shimadzu Class-VP System (LC-10 ADVP/SCL-10AVP/SPD-M10AVP/CT010ACVP/DGU12A); column: CHIRALPAK AD-H (0.46 cm×25 cm); flow rate: 1.0 mL/min; elution solvent: ethanol (100%, isocratic); detection: UV (254 nm)

Isomer B: (+)-1,4-dimethyl-N-[4-(methylsulfonyl)phenyl]-5-[2-(trifluoromethyl)phenyl]-1H-pyrrole-3-carboxamide $[α]_D^{22}$: +18° (c=1.2, EtOH).
$^1$H-NMR (500 MHz, CDCl$_3$) δ: 7.91 (2H, d, J=8.8 Hz), 7.85-7.80 (3H, m), 7.68-7.64 (2H, m), 7.61 (1H, t, J=7.3 Hz), 7.35 (1H, d, J=7.3 Hz), 7.31 (1H, s), 3.33 (3H, s), 3.06 (3H, s), 2.10 (3H, s).

HR-MS (ESI) calcd for C$_{21}$H$_{20}$F$_3$N$_2$O$_3$S [M+H]$^+$, required m/z: 437.1147, found: 437.1153.

Retention time: 6.3 min.

Example 3

(+/−)-1-(2-hydroxyethyl)-4-methyl-N-[4-(methylsulfonyl)phenyl]-5-[2-(trifluoromethyl)phenyl]-1H-pyrrole-3-carboxamide After methyl 4-methyl-5-[2-(trifluoromethyl)phenyl]-1H-pyrrole-3-carboxylate was obtained by the method described in Example 16 of WO 2006/012642, the following reaction was performed using this compound as a raw material.

Methyl 4-methyl-5-[2-(trifluoromethyl)phenyl]-1H-pyrrole-3-carboxylate (1.4 g, 4.9 mmol) was dissolved in methanol (12 mL), and a 5 M aqueous sodium hydroxide solution (10 mL) was added thereto, and the resulting mixture was heated under reflux for 3 hours. After the mixture was cooled to room temperature, formic acid (5 mL) was added thereto to stop the reaction. After the mixture was concentrated under reduced pressure, water (10 mL) was added thereto to suspend the resulting residue. The precipitated solid was collected by filtration and washed times with water. The obtained solid was dried under reduced pressure, whereby 4-methyl-5-[2-(trifluoromethyl)phenyl]-1H-pyrrole-3-carboxylic acid (1.1 g, 83%) was obtained as a solid. The thus obtained solid was suspended in dichloromethane (10 mL), oxalyl chloride (0.86 mL, 10 mmol) was added thereto, and the resulting mixture was stirred at room temperature for 2 hours. After the mixture was concentrated under reduced pressure, the residue was dissolved in tetrahydrofuran (10 mL), and 4-(methylsulfonyl)aniline hydrochloride (1.0 g, 4.9 mmol) and N,N-diisopropylethylamine (2.8 mL, 16 mmol) were sequentially added to the solution, and the resulting mixture was heated under reflux for 18 hours. After the mixture was cooled to room temperature, the solvent was distilled off under reduced pressure, and acetonitrile (10 mL) and 3 M hydrochloric acid (100 mL) were added to the residue. A precipitated solid was triturated, collected by filtration and washed with water, and then, dried under reduced pressure, whereby 4-methyl-N-[4-(methylsulfonyl)phenyl]-5-[2-(trifluoromethyl)phenyl]-1H-pyrrole-3-carboxamide (1.4 g, 89%) was obtained as a solid.

$^1$H-NMR (400 MHz, DMSO-d6) δ11.34 (1H, brs,), 9.89 (1H, s), 7.97 (2H, d, J=6.6 Hz), 7.87-7.81 (3H, m), 7.73 (1H, t, J=7.4 Hz), 7.65-7.61 (2H, m), 7.44 (1H, d, J=7.8 Hz), 3.15 (3H, s), 2.01 (3H, s).

Sodium hydride (0.12 g, 3 mmol, 60% dispersion in mineral oil) was dissolved in N,N-dimethylformamide (1.5 mL), and 4-methyl-N-[4-(methylsulfonyl)phenyl]-5-[2-(trifluoromethyl)phenyl]-1H-pyrrole-3-carboxamide (0.47 g, 1.1 mmol) was added thereto, and then, the resulting mixture was stirred at room temperature for 30 minutes. Then, 1,3,2-dioxathiolane-2,2-dioxide (0.14 g, 1.2 mmol) was added thereto, and the resulting mixture was stirred at room temperature. After 1 hour, sodium hydride (40 mg, 1.0 mmol, oily, 60%) was added thereto again, and the resulting mixture was stirred for 30 minutes. Then, 1,3,2-dioxathiolane-2,2-dioxide (12 mg, 0.11 mmol) was added thereto, and the resulting mixture was stirred at room temperature for 1 hour. After the mixture was concentrated under reduced pressure, methanol (5 mL) was added to the residue and insoluble substances were removed by filtration, and the filtrate was concentrated again. To the residue, tetrahydrofuran (2 mL) and 6 M hydrochloric acid (2 mL) were added, and the resulting mixture was stirred at 60° C. for 16 hours. The reaction was cooled to room temperature, and then dissolved in ethyl acetate, and washed with water and saturated saline. The organic layer was dried over anhydrous sodium sulfate and filtered. Then, the filtrate was concentrated under reduced pressure, and the residue was purified by silica gel column chromatography (ethyl acetate), whereby the objective compound (0.25 g, 48%) was obtained.

$^1$H-NMR (400 MHz, CDCl$_3$) δ: 7.89-7.79 (m, 6H), 7.66-7.58 (m, 2H), 7.49 (s, 1H), 7.36 (d, 1H, J=7.4 Hz), 3.81-3.63 (m, 4H), 3.05 (s, 3H), 2.08 (s, 3H).

HR-MS (ESI) calcd for $C_{22}H_{22}F_3N_2O_4S$ [M+H]$^+$, required m/z: 467.1252, found: 467.1246.

Anal. calcd for $C_{22}H_{21}F_3N_2O_4S$: C, 56.65; H, 4.54; N, 6.01; F, 12.22; S, 6.87. found: C, 56.39; H, 4.58; N, 5.99; F, 12.72; S, 6.92.

Example 4

Optical Resolution of Compound of Example 3

Resolution was performed 4 times in the same manner as in Example 2, whereby 74 mg of Isomer C was obtained as a solid from a fraction containing Isomer C ($t_R$=10 min), and 71 mg of Isomer D was obtained as a solid from a fraction containing Isomer D ($t_R$=11 min).

Isomer C: (+)-1-(2-hydroxyethyl)-4-methyl-N-[4-(methylsulfonyl)phenyl]-5-[2-(trifluoromethyl)phenyl]-1H-pyrrole-3-carboxamide $[α]_D^{21}$: +7.1° (c=1.0, EtOH).
$^1$H-NMR (400 MHz, CDCl$_3$) δ: 7.91 (s, 1H), 7.87-7.79 (m, 5H), 7.67-7.58 (m, 2H), 7.51 (s, 1H), 7.35 (d, 1H, J=7.0 Hz), 3.78-3.65 (m, 4H), 3.05 (s, 3H), 2.07 (s, 3H).

HR-MS (ESI) calcd for $C_{22}H_{22}F_3N_2O_4S$ [M+H]$^+$, required m/z: 467.1252, found: 467.1260.

Retention time: 4.0 min.

Isomer D: (−)-1-(2-hydroxyethyl)-4-methyl-N-[4-(methylsulfonyl)phenyl]-5-[2-(trifluoromethyl)phenyl]-1H-pyrrole-3-carboxamide $[α]_D^{21}$: −7.2° (c=1.1, EtOH).
$^1$H-NMR (400 MHz, CDCl$_3$) δ: 7.88-7.79 (m, 6H), 7.67-7.58 (m, 2H), 7.50 (s, 1H), 7.36 (d, 1H, J=7.5 Hz), 3.79-3.65 (m, 4H), 3.05 (s, 3H), 2.08 (s, 3H).

HR-MS (ESI) calcd for $C_{22}H_{22}F_3N_2O_4S$ [M+H]$^+$, required m/z: 467.1252, found: 467.1257.

Retention time: 4.5 min.

Example 5

(+/−)-1-(2-hydroxyethyl)-5-[4-methoxy-2-(trifluoromethyl)phenyl]-4-methyl-N-[4-(methylsulfonyl)phenyl]-1H-pyrrole-3-carboxamide The compound was synthesized by the method described in WO 2006/012642.

$^1$H-NMR (500 MHz, CDCl$_3$) δ: 7.91 (2H, d, J=8.3 Hz), 7.82 (2H, d, J=8.3 Hz), 7.69 (1H, s), 7.46 (1H, s), 7.32 (1H, d, J=2.0 Hz), 7.28-7.27 (1H, m), 7.14 (1H, dd, J=8.3 and 2.0 Hz), 3.92 (3H, s), 3.82-3.66 (4H, m), 3.06 (3H, s), 2.10 (3H, s).

HR-MS (ESI) calcd for $C_{23}H_{24}F_3N_2O_5S$ [M+H]$^+$, required m/z: 497.1358, found: 497.1361.

Example 6

Optical Resolution of Compound of Example 5

Resolution was performed 7 times in the same manner as in Example 2, whereby 50 mg of Isomer E was obtained as a solid from a fraction containing Isomer E ($t_R$=11 min), and 41 mg of Isomer F was obtained as a solid from a fraction containing Isomer F ($t_R$=14 min).

Isomer E: (−)-1-(2-hydroxyethyl)-5-[4-methoxy-2-(trifluoromethyl)phenyl]-4-methyl-N-[4-(methylsulfonyl)phenyl]-1H-pyrrole-3-carboxamide $[α]_D^{22}$−1.3° (c=1.0, EtOH).
$^1$H-NMR (500 MHz, CDCl$_3$) δ: 7.90 (2H, d, J=8.3 Hz), 7.83-7.79 (3H, m), 7.48 (1H, s), 7.32 (1H, d, J=2.4 Hz), 7.28-7.25 (1H, m), 7.14 (1H, dd, J=8.3 and 2.4 Hz), 3.92 (3H, s), 3.81-3.65 (4H, m), 3.06 (3H, s), 2.09 (3H, s), 1.82 (1H, brs).

HR-MS (ESI) calcd for $C_{23}H_{24}F_3N_2O_5S$ [M+H]$^+$, required m/z: 497.1358, found: 497.1359.

Retention time: 4.1 min.

Isomer F: (+)-1-(2-hydroxyethyl)-5-[4-methoxy-2-(trifluoromethyl)phenyl]-4-methyl-N-[4-(methylsulfonyl)phenyl]-1H-pyrrole-3-carboxamide $[α]_D^{23}$: +1.6° (c=0.8, EtOH).
$^1$H-NMR (500 MHz, CDCl$_3$) δ: 7.91 (2H, d, J=8.8 Hz), 7.81 (2H, d, J=8.8 Hz), 7.69 (1H, s), 7.46 (1H, s), 7.32 (1H, d, J=2.4 Hz), 7.28-7.25 (1H, m), 7.14 (1H, dd, J=8.3 and 2.4 Hz), 3.92 (3H, s), 3.82-3.66 (4H, m), 3.05 (3H, s), 2.09 (3H, s).

HR-MS (ESI) calcd for $C_{23}H_{24}F_3N_2O_5S$ [M+H]$^+$, required m/z: 497.1358, found: 497.1340.

Retention time: 4.7 min.

Test Example 1

A plasmid pM-hMR-LBD which is obtained by ligation of a ligand-binding domain (LBD, corresponding to a region of about 308 amino acids at the carboxy terminus) of human mineralocorticoid receptor (hMR, NM_000901) to a DNA-binding domain (corresponding to a region of 147 amino acids at the amino terminus) of a yeast transcription factor GAL4 and expresses GAL4-hMR receptor was constructed. Using a reporter plasmid which has a sequence binding to the DNA-binding domain of GAL4 (UAS sequence) and contains a luciferase gene (such as pFR-Luc, a plasmid available from Stratagene Cloning Systems), a reporter assay was performed.

The previously obtained plasmid pM-hMR-LBD and the reporter plasmid were transfected into a human fetus-derived renal cell line HEK293 by the lipofection method. On the following day, the cells were treated with trypsin and collected. A white 96-well plate (manufactured by Costar, Inc.) was prepared, and the cells were dispensed into each well in an amount of 95 μL using a DMEM medium containing 5% FBS (fetal bovine serum) which had been treated with activated charcoal.

As for each test compound, solutions obtained by dissolving the test compound in dimethyl sulfoxide at predetermined concentrations were used, and the solutions were appropriately diluted with medium and added to the cells in the white 96-well plate to give a final concentration of 0.1%. When the test compound was added, 1 nM aldosterone was allowed to be present. A well group to which dimethyl sulfoxide was added was assigned Control 1 group; and a well group to which 1 nM aldosterone was added was assigned Control 2 group. After the addition, the plate was incubated overnight.

On the following day, the medium was removed, and a luciferase substrate (Wako Pure Chemical Industries, Ltd.) was prepared according to the package insert and added to each well in an amount of 50 μL, and then, the plate was stirred for about 30 minutes. The luminescence intensity of each well was measured using Analyst (manufactured by Molecular Devices Corporation) and taken as the luciferase activity. The luciferase activity value of Control 1 group was taken as 0%, the luciferase activity value of Control 2 group was taken as 100%, and relative luciferase activity values for the respective doses of the test compound in the test compound addition group were plotted to create a graph. From the graph, the maximum value was calculated as Imax (%), and the concentration of the test compound showing the value of Imax/2 was calculated as ICmax50 (M). In Table 1, ICmax50 values are shown.

(Results) As shown in the following Table 1, the atropisomer of the invention showed remarkable mineralocorticoid receptor antagonistic activity as compared with the corresponding racemic compound.

TABLE 1

| Test compound | ICmax50 (nM) | Imax (%) |
| --- | --- | --- |
| Compound of Example 1 | 13 | 95 |
| Isomer A | >1000 | N.D. [1] |
| Isomer B | 2.6 | 123 |
| Compound of Example 3 | 5.3 | 105 |
| Isomer C | >1000 | N.D. [1] |
| Isomer D | 2.4 | 99 |
| Compound of Example 5 | 5.3 | 97 |
| Isomer E | 1.8 | 115 |
| Isomer F | >1000 | N.D. [1] |

[1] Not Determined

Test Example 2

Cynomolgus monkeys (male) were used, and the monkeys were fasted from one day before the test compound was administered. The administration sample was prepared by adding a 0.5% MC (methyl cellulose) solution to the test compound such that the dose was 3 mg/2 mL/kg. Each administration sample was administered to the stomach of the cynomolgus monkey using a tube. After the sample was administered, about 5 mL of water was administered. Each administration sample was administered to three cynomolgus monkeys in one group.

As for blood collection, about 1 mL of blood was collected from the femoral vein before administration, and minutes and 1, 2, 4, 6, 8, 24 and 48 hours after administration using an injection syringe treated with heparin. The collected blood was centrifuged (15,000×g, min, 4° C.) to obtain plasma. The obtained plasma was stored in a freezer (−20° C.) until pretreatment.

Preparation of Standard Solution and Internal Standard (IS) Solution: Each test compound was dissolved in acetonitrile, whereby a 1 mg/mL solution of each test compound was prepared. A standard solution was prepared by diluting each compound solution with acetonitrile. Further, sodium warfarin (Wako Pure Chemical Industries, Ltd.) was dissolved in acetonitrile to prepare a 500 ng/mL IS solution.

Pretreatment of Plasma Sample: 50 μL of the plasma sample was taken out and 50 μL of acetonitrile was added thereto. For a calibration curve, 50 μL of each standard solution (acetonitrile solution) was added to 50 μL of the blank plasma. To all the samples, 150 μL of the IS acetonitrile solution was added, and the mixture was stirred, and then centrifuged (about 1,800×g, 30 min, 4° C.). After filtration was performed with Sirocco Protein Precipitation Plate (Waters Corporation), the filtrate was appropriately diluted with a mobile phase to prepare an LC-MS/MS analysis sample.

Determination of Test Compound: The plasma concentration of each test compound was analyzed by the LC-MS/MS method.

[HPLC Analysis Conditions]
HPLC: LC-10Avp series: Prominence (Shimadzu Corporation)
Column: X-Bridge RP18, 2.0 mm I.D.×50 mm, 2.5 μm (Waters Corporation)
Mobile phase: A=10 mM aqueous ammonium formate solution, B=acetonitrile

[MS/MS Analysis Conditions]
MS: API 4000 (AB/MDS SCIEX, Inc.)
Ionization Method Turbo ion spray (Positive or Negative)
Ionization Mode: Atmospheric pressure chemical ionization (APCI)
Detection Mode: MRM Analysis: A pharmacokinetics parameter was calculated from the plasma concentration of each agent using WinNonlin Professional (Ver. 4.0.1, Pharsight Corporation). Incidentally, Noncompartment model was used as a model for calculation of the parameter.

(Results) The compounds of Example 1, Isomer B of Example 2, Example 3, Isomer D of Example 4, Example 5 and Isomer E of Example 6 were evaluated. As a result, as shown in Table 2, Isomer B, Isomer D and Isomer E, which are atropisomers with high activity demonstrated in Test Example 1 significantly improved the plasma concentration as compared with the compounds of Example 1, Example 3 and Example 5 which are the corresponding racemic compounds, respectively.

TABLE 2

| Test compound | AUC [1] (ng · h/mL) | Cmax [2] (ng/mL) |
| --- | --- | --- |
| Example 1 | 860 | 42 |
| Isomer B | 3446 | 184 |
| Example 3 | 7667 | 380 |
| Isomer D | 26390 | 1330 |
| Example 5 | 33 | 2 |
| Isomer E | 7187 | 681 |

[1] AUC (ng · h/mL): Area under the plasma concentration (measured by LC-MS/MS method) versus time curve (0-48 hr.);
[2] Cmax (ng/mL): Maximum concentration Formulation Example 1

Capsule

| | |
|---|---|
| Isomer B | 50.0 mg |
| Lactose | 128.7 |
| Cornstarch | 70.0 |
| Magnesium stearate | 1.3 |
| | 250 mg |

Powder of the above formulation was mixed, and after the mixture was passed through a sieve of 60 mesh, the powder was filled in a No. 3 gelatin capsule of 250 mg to prepare a capsule.

Preparation Example 2

Tablet

| | |
|---|---|
| Isomer D | 50.0 mg |
| Lactose | 124.0 |
| Cornstarch | 25.0 |
| Magnesium stearate | 1.0 |
| | 200 mg |

Powder of the above formulation was mixed and tabletted with a tabletting machine to prepare a tablet (200 mg per tablet).

INDUSTRIAL APPLICABILITY

The atropisomer of a compound having the general formula (I) of the invention shows particularly excellent pharmacological activities such as a mineralocorticoid receptor antagonistic activity, an antihypertensive activity, a vasodilatory activity, a cardioprotective activity, a nephropathy inhibitory activity, an antiarteriosclerotic activity and a diuretic activity, and also is highly safe, therefore it is useful as a prophylactic or therapeutic agent for hypertension, angina pectoris, acute coronary syndrome, congestive heart failure, nephropathy, arteriosclerosis, cerebral infarction, fibrosis or primary aldosteronism.

The invention claimed is:

1. (−)-1-(2-hydroxyethyl)-4-methyl-N-[4-(methylsulfonyl)phenyl]-5-[2-(trifluoromethyl)phenyl]-1H-pyrrole-3-carboxamide.

2. (+)-1,4-dimethyl-N-[4-(methylsulfonyl)phenyl]-5-[2-(trifluoromethyl)phenyl]-1H-pyrrole-3-carboxamide.

3. (−)-1-(2-hydroxyethyl)-5-[4-methoxy-2-(trifluoromethyl)phenyl]-4-methyl-N-[4-(methylsulfonyl)phenyl]-1H-pyrrole-3-carboxamide.

4. A pharmaceutical consisting of the atropisomer according to any one of claims 1, 2, or 3 as an active ingredient.

5. A pharmaceutical composition comprising the atropisomer according to any one of claims 1, 2, or 3 and a pharmacologically acceptable carrier.

6. The composition of claim 5 in the form of a tablet, a capsule, a granule, a powder, a syrup, an injection, a suppository, or a plaster.

* * * * *

UNITED STATES PATENT AND TRADEMARK OFFICE
CERTIFICATE OF CORRECTION

PATENT NO. : 8,524,918 B2  
APPLICATION NO. : 12/576091  
DATED : September 3, 2013  
INVENTOR(S) : Aoki et al.

Page 1 of 1

It is certified that error appears in the above-identified patent and that said Letters Patent is hereby corrected as shown below:

In the Specification

| COLUMN | LINE | |
|---|---|---|
| 2 | 29 | "a pair atropisomers" should read --a pair of atropisomers-- |
| 2 | 44 | "(8)(-)-1-(2-hydroxyethyl)" should read --(8) (-)-1-(2-hydroxyethyl)-- |
| 2 | 47 | "(9)(+)-1,4-dimethyl" should read --(9) (+)-1,4-dimethyl-- |
| 2 | 49 | "(10)(-)-1-(2-hydroxyethyl)" should read --(10) (-)-1-(2-hydroxyethyl)-- |
| 6 | 7 | "/CT010ACVP/" should read --/CTO10ACVP/-- |
| 6 | 10 | After "(254 nm)" insert --.-- |
| 6 | 44 | "washed times" should read --washed 3 times-- |
| 6 | 61 | after "then" delete "," |
| 10 | 2 | "and minutes" should read --and 30 minutes-- |
| 10 | 5 | "(15,000×g, min," should read --(15,000×g, 3 min,-- |
| 10 | 37 | after "Ionization Method" insert --:-- |

Signed and Sealed this  
Third Day of June, 2014

Michelle K. Lee  
*Deputy Director of the United States Patent and Trademark Office*